US012599301B2

(12) United States Patent
Chan et al.

(10) Patent No.: US 12,599,301 B2
(45) Date of Patent: Apr. 14, 2026

(54) SYSTEM FOR CONDUCTING EYE EXAMINATIONS FOR VISUAL ACUITY

(71) Applicant: Verily Life Sciences LLC, Dallas, TX (US)

(72) Inventors: Jeremy Chan, San Jose, CA (US); Supriyo Sinha, Menlo Park, CA (US)

(73) Assignee: Verily Life Sciences LLC, Dallas, TX (US)

( * ) Notice: Subject to any disclaimer, the term of this patent is extended or adjusted under 35 U.S.C. 154(b) by 288 days.

(21) Appl. No.: 18/390,315

(22) Filed: Dec. 20, 2023

(65) Prior Publication Data

US 2025/0204771 A1 Jun. 26, 2025

(51) Int. Cl.
*A61B 3/032* (2006.01)
*A61B 3/00* (2006.01)
*A61B 3/14* (2006.01)

(52) U.S. Cl.
CPC ............ *A61B 3/032* (2013.01); *A61B 3/0025* (2013.01); *A61B 3/005* (2013.01); *A61B 3/14* (2013.01)

(58) Field of Classification Search
CPC ....... A61B 3/032; A61B 3/0025; A61B 3/005; A61B 3/14
USPC ........................................ 351/223, 222, 206
See application file for complete search history.

(56) References Cited

U.S. PATENT DOCUMENTS 5,191,897 A 3/1993 Meshel
6,179,421 B1 * 1/2001 Pang ........................ A61B 3/12
351/205

7,976,162 B2 7/2011 Flitcroft
10,470,654 B2 * 11/2019 Schmid ................ A61B 3/0041
11,432,718 B2 9/2022 Xu
2013/0128229 A1 5/2013 Huang
2016/0184170 A1 6/2016 Bunker
2018/0103841 A1 4/2018 Sprowl
2019/0012784 A1 * 1/2019 Wiley .................... G16H 10/60
2019/0046029 A1 2/2019 Tomasi et al.
(Continued)

FOREIGN PATENT DOCUMENTS

CN 109464118 A 3/2019
WO 2020176784 A1 9/2020

OTHER PUBLICATIONS

PCT International Search Report and Written Opinion mailed Feb. 7, 2025, in corresponding International Application No. PCT/US2024/060737, 13 pages.

*Primary Examiner* — William R Alexander
(74) *Attorney, Agent, or Firm* — Christensen O'Connor Johnson Kindness PLLC

(57) ABSTRACT

Systems, devices, and methods for conducting an eye examination for visual acuity are provided. In one example, a system may include an optical subsystem positioned in front of one or both eyes of a user. The optical subsystem may comprise a handheld device or a head worn device, a visual indicator, and a plurality of vision modifiers. The system may determine a distance between the optical subsystem and the display based on comparing a fixed size of the visual indicator to a detected size of the visual indicator in an image obtained by a camera. The system may output an eye examination image for visual acuity based on the distance being within a valid range. The eye examination image may include a visual stimulus having an output size determined based on the distance. The system may receive an input from the user indicating a selection of the visual stimulus.

22 Claims, 7 Drawing Sheets

(56)　　　　　　　References Cited

U.S. PATENT DOCUMENTS

| | | | |
|---|---|---|---|
| 2019/0082951 A1* | 3/2019 | Merriam | A61B 3/032 |
| 2019/0110679 A1* | 4/2019 | Mackool | A61B 3/032 |
| 2019/0133437 A1* | 5/2019 | Sugawara | G02B 27/18 |
| 2020/0069173 A1* | 3/2020 | Jensen | A61B 3/024 |
| 2020/0178792 A1* | 6/2020 | Mackool | A61B 3/063 |
| 2020/0285062 A1 | 9/2020 | Grutman et al. | |
| 2022/0117695 A1* | 4/2022 | Weissman | A61B 90/37 |
| 2022/0133212 A1* | 5/2022 | Krueger | A61B 3/0041 |
| | | | 600/301 |
| 2023/0004008 A1* | 1/2023 | Samec | A61B 8/10 |
| 2025/0072743 A1 | 3/2025 | Kalamkar et al. | |

* cited by examiner

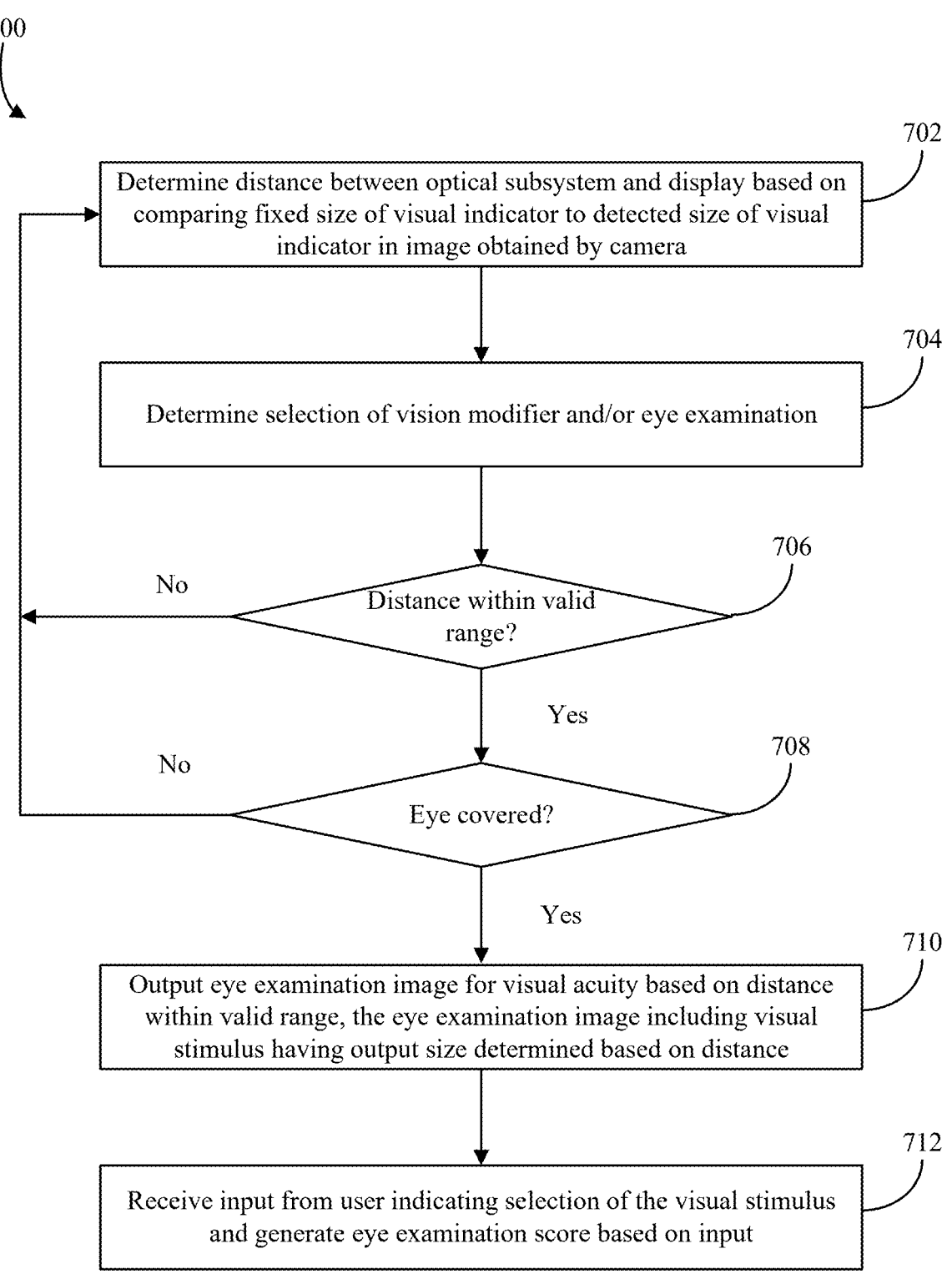

700

702

Determine distance between optical subsystem and display based on comparing fixed size of visual indicator to detected size of visual indicator in image obtained by camera

704

Determine selection of vision modifier and/or eye examination

706

Distance within valid range?

No

Yes

708

No

Eye covered?

Yes

710

Output eye examination image for visual acuity based on distance within valid range, the eye examination image including visual stimulus having output size determined based on distance

712

Receive input from user indicating selection of the visual stimulus and generate eye examination score based on input

FIG. 7

SYSTEM FOR CONDUCTING EYE EXAMINATIONS FOR VISUAL ACUITY

This disclosure relates generally to utilizing a computing device for an eye examination and, more specifically, to a system for conducting eye examinations for visual acuity. Other aspects are also described.

BACKGROUND

An occluder is a structure that may be used during the administration of an eye examination (e.g., an eye test, such as a test for visual acuity). An occluder can be configured to block all light (e.g., a complete occluder) or a portion of light (e.g., a pinhole occluder) to an eye of a patient. Blocking the light in various ways may enable different types of eye examinations to be performed, such as eye examinations for distance acuity (e.g., measuring how well a patient can see objects at a distance), pinhole acuity (e.g., testing a patient for uncorrected refractive errors), and near visual acuity (e.g., measuring how well a patient can see objects close up).

SUMMARY

Implementations of this disclosure include utilizing a system for conducting an eye examination for visual acuity, including an optical subsystem configured to be positioned in front of one or both eyes of a user and a depth estimation algorithm to determine a distance between the optical subsystem and a display used to output the eye examination. The optical subsystem may comprise a handheld device or a head worn device (e.g., goggles, enabling hands free), a visual indicator having a fixed size, and a plurality of vision modifiers configured to modify vision of the user. The system may also include a camera, a display, and one or more processors configured by instructions stored in memory. The system may determine, via the camera, a distance between the optical subsystem and the display. The distance may be determined based on comparing the fixed size of the visual indicator to a detected size of the visual indicator in an image obtained by the camera. The system may output, via the display, an eye examination image for visual acuity based on the distance being within a valid range. The eye examination image may include a visual stimulus having an output size determined based on the distance. The system may receive an input from the user indicating a selection of the visual stimulus and may generate an eye examination score based on the input. Other aspects are also described and claimed.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

FIG. 7 is a flowchart of an example of a process for conducting eye examinations for visual acuity.

DETAILED DESCRIPTION

Figure 1:
FIG. 1 is a block diagram of an example of system for conducting eye examinations for visual acuity.

A user can utilize a computing device, such as handheld computer running a program or application (e.g., a smartphone or tablet computer), to self-administer an eye examination. For example, the eye examination could be an eye test for visual acuity, astigmatism, or color blindness. Conducting an eye examination for visual acuity involves positioning the user at a known distance from a visual stimulus associated with the eye examination. For example, a Snellen chart is an eye chart that can be used to measure visual acuity. When testing a user via a Snellen chart, the user may be positioned a distance away from the chart to read letters (e.g., the visual stimulus) of different sizes in different rows. However, if the user is too close or too far away from the chart, the test might not generate accurate results.

In some cases, a user may be positioned at a known distance from a display screen to conduct an eye examination. Such cases may involve a physical structure to maintain the distance. For example, a viewer having a known length may be attached to the display. A user may position their eye over the viewer and the system can conduct the eye examination based on the known length. In another example, the display may be attached to a google or headset that is worn by the user. The system can then conduct the eye examination based on known dimensions of the headset. However, such structures involving attachment to screens may be cumbersome for patients to use. It is therefore desirable to provide a system for conducting eye examinations for visual acuity while simplifying the system for users.

Implementations of this disclosure address problems such as these by utilizing a system for conducting an eye examination for visual acuity, including an optical subsystem configured to be positioned in front of one or both eyes of a user (e.g., a patient) and a depth estimation algorithm to determine a distance between the optical subsystem and a display used to output the eye examination. The optical subsystem may comprise a handheld device or a head worn device (e.g., different form factors), a visual indicator having a fixed size, and a plurality of vision modifiers configured to modify vision of the user. The system may also include a camera, a display, and one or more processors configured by instructions stored in memory. The system may determine, via the camera, a distance between the optical subsystem and the display. The distance may be determined based on comparing the fixed size of the visual indicator (e.g., stored in a data structure) to a detected size of the visual indicator in an image obtained by the camera. The system may output, via the display, an eye examination image for visual acuity based on the distance being within a valid range. The eye examination image may include a visual stimulus having an output size determined based on the distance. The system may receive an input from the user indicating a selection of the visual stimulus and may generate an eye examination score based on the input. As a result, eye examinations can be administered to users while reducing inconvenience to users.

In some implementations, the system may include a vision modifier for visual acuity testing. The system may enable users to self-administer a visual acuity test, including without administration by a trained person. A display may be used to display various stimuli. The user, following instructions on the display while holding the handheld device or wearing the head worn device (e.g., the device placed in line of either or both eyes), can modify their vision for the eye testing. In some implementations, a combination of the display, an input device, and the handheld device or the head worn device, including with combinations of vision modifiers, can provide the screening and diagnostic services. In some implementations, the vision modifiers can be combined and placed in front of the user, without user intervention, by wired or wireless communication with the display or another device. In some implementations, the display and input device can be combined as a single device (e.g., a user device, such as smartphone, tablet, or laptop computer). In some implementations, the vision modifiers can include any combination of a pass through (e.g., nothing), one or more occluders, one or more lenses, and/or one or more filters. In some implementations, the user can select the vision modifier (e.g., via an optical subsystem), and the system (e.g., an eye examination subsystem) can detect the selection and output an eye examination image to the display based on the selection. In some implementations, the system (e.g., the eye examination subsystem) can select an eye examination image to display based on an eye examination to perform, then cause a vision modifier to be selected (e.g., causing the optical subsystem to automatically switch to the vision modifier based on a transmission from the eye examination subsystem).

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

FIG. 1 is a block diagram of an example of system 100 for conducting eye examinations for visual acuity. The system 100 may include an optical subsystem 102 and an eye examination subsystem 104. The optical subsystem 102 may be configured to be positioned in front of one or both eyes of a user. In some cases, the optical subsystem 102 may comprise a handheld device configured to be held by a hand of the user (e.g., FIGS. 2 and 3). In some cases, the optical subsystem 102 may comprise a head worn device configured to be worn on the head of the user (e.g., FIGS. 4 and 5). The optical subsystem 102 may include a visual indicator 106 having a fixed size that may correspond to a number of pixels in an image. For example, the visual indicator 106 could be a QR code, barcode, or another visual symbol, and in some cases, may comprise an anatomic feature of the user, such as the user's eye or part of the eye (e.g., the iris). The optical subsystem 102 may also include a plurality of vision modifiers 108 to modify vision of the user in different ways, such as a pass through (nothing), one or more occluders, one or more lenses, and/or one or more filters. In some implementations, the optical subsystem 102 may also include a control system 110 comprising one or more processors configured to execute instructions stored in memory, and/or a wired or wireless communications system.

The eye examination subsystem 104 may include a camera 112, a display 114, an input device 116, a control system 118, and/or a data structure 120. In some implementations, the eye examination subsystem 104 may be integrated in a user device, such as a handheld computer (e.g., a smartphone, tablet, or laptop computer) running a program or application. For example, the camera 112 may be a front facing built-in camera of a user device oriented toward the user. The display 114 may be a front facing built-in touchscreen of the user device oriented toward the user and positioned relatively close to the user's eyes and face, e.g., within an arm's length. The display 114 may be used to output an eye examination image, including a visual stimulus. The input device 116 may comprise a touchscreen (e.g., the display 114) or a microphone of the user device to receive voice commands from the user. In some implementations, the input device 116 may comprise a separate device from the user device, such as an air mouse or a laser device. The input device 116 may be used to receive an input from the user indicating a selection of the visual stimulus. The control system 118 may include one or more processors configured to execute instructions stored in memory, and/or a wired or wireless communications system, including to communicate with the data structure 120 and/or the optical subsystem 102 (e.g., via the control system 110). The data structure 120 may store data for conducting eye examinations, such as one or more tables indicating relationships between types of eye examinations, types of vision modifiers, and types of visual indicators with known or fixed sizes.

The system 100 (e.g., via the control system 118 and/or the control system 110) may execute a depth estimation algorithm to determine a distance between the optical subsystem 102 and the display 114. The system 100 may determine, via the camera 112, a distance between the optical subsystem 102 and the display 114. The distance may be determined based on comparing a fixed size of the visual indicator 106 (e.g., determined from the data structure 120) to a detected size of the visual indicator 106 in an image obtained by the camera 112. For example, the system 100 may calculate an amount in which the detected size of the visual indicator 106 (e.g., a number of pixels in the image) is smaller or larger than a known size of the visual indicator 106 (e.g., stored in the data structure 120), then estimate the distance between the optical subsystem 102 and the display 114 based on the calculation. The system 100 may then determine whether the distance is within a valid range (e.g., +/− an amount of a predetermined distance, such as +/−5 centimeters of a distance of 60 centimeters), then output, via the display 114, an eye examination image for visual acuity based on the distance being within the valid range. The system 100 may also determine an output size of a visual stimulus of the eye examination image based on the distance (e.g., a number of pixels), then output the visual stimulus at the output size. The system 100 may then receive an input from the user, via the input device 116, indicating a selection of the visual stimulus (e.g., a lowest line that the user can read). The system 100 may then generate an eye examination score based on the input.

Figure 2:
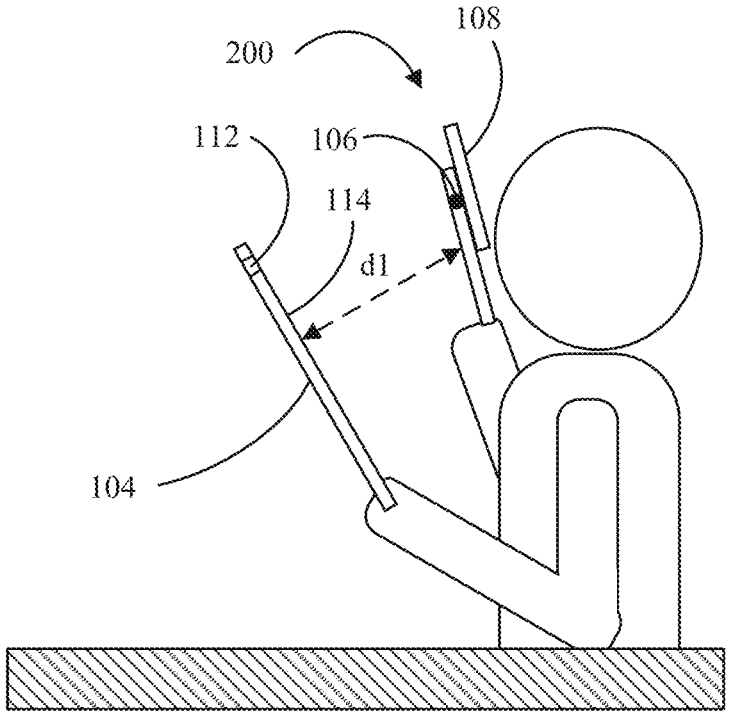
FIG. 2 is an example of utilizing an optical subsystem comprising a handheld device for conducting eye examinations for visual acuity.

For example, with additional reference to FIG. 2, the user can utilize a handheld device 200 (e.g., a first variation of the optical subsystem 102) for conducting eye examinations. The handheld device 200 may enable the user to self-administer an eye examination, such as a visual acuity test, astigmatism test, or color test displayed via the display 114. The eye examination may require that one of the user's eyes remains open while the other of the user's eyes is closed. In some cases, the user may hold the handheld device 200 against the user's face while holding or resting the eye examination subsystem 104 (e.g., the user device) within an arm's length. The system 100 may determine, via the camera 112, a distance d1 between the handheld device 200 and the display 114. The distance d1 may be determined based on comparing a fixed size of the visual indicator 106 to a detected size of the visual indicator 106 in an image obtained by the camera 112.

Figure 3:
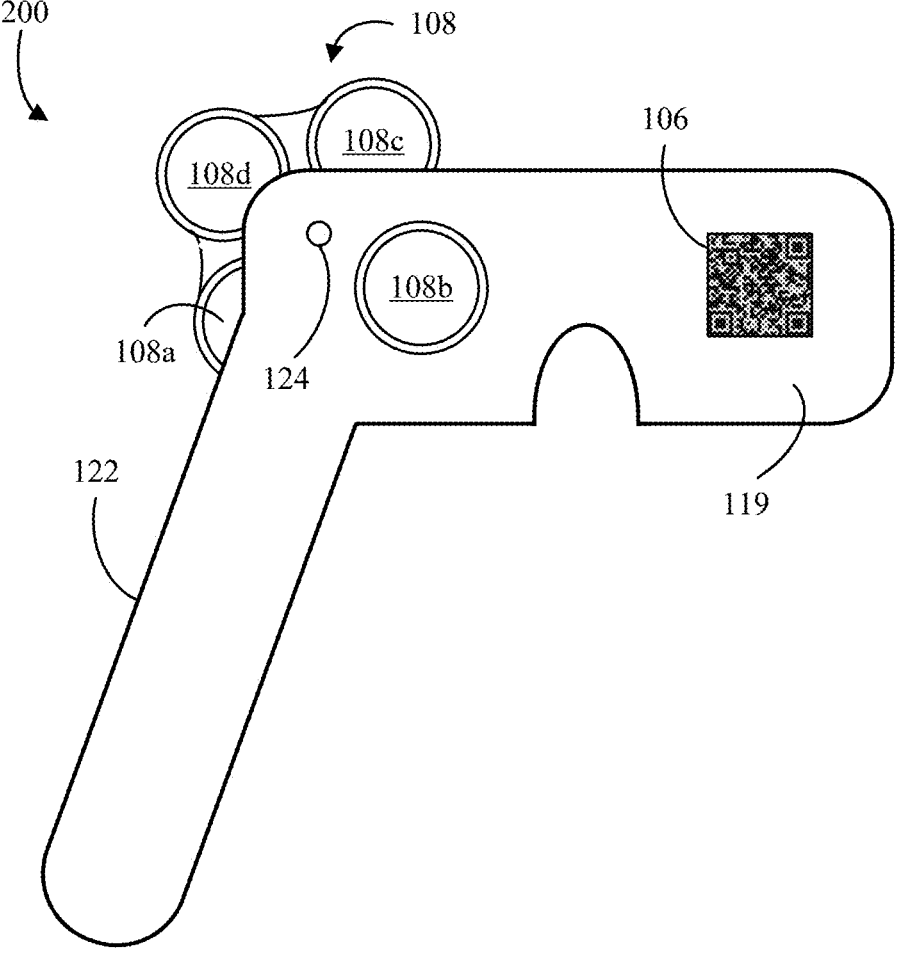
FIG. 3 is an example of a handheld device.

With further reference to FIG. 3, the handheld device 200 may include the visual indicator 106 for depth estimation. In some cases, the user may obtain the handheld device 200 via parcel post or mail upon registration via the program or application. The visual indicator 106 could be a QR code, barcode, or other visual symbol, such as one or more letters, geometrical shapes, text, images, or colors. In some cases, the visual indicator 106 may be printed or formed on an adhesive label that is attached to the body of the handheld device 200, such as in a position corresponding to an eye that is occluded. In some implementations, the visual indicator 106 may encode information about the handheld device 200, such as configurations of one or more of the plurality of vision modifiers 108. For example, the visual indicator 106 may comprise a code that indicates a selection of a vision modifier of the plurality of vision modifiers 108.

The handheld device 200 may include an opaque surface 119 that blocks light to one of the user's eyes. For example, as shown in FIG. 3, the left eye of the user may be occluded by the opaque surface 119. The handheld device 200 can help the user to ensure that the correct eye is properly closed (e.g., the untested eye, such as the left eye) when performing the eye examination. The handheld device 200 may include the plurality of vision modifiers 108 to modify vision of the user's other eye in different ways, such as a pass through (nothing), one or more occluders, one or more lenses, and/or one or more filters. For example, the plurality of vision modifiers 108 may include a pinhole occluder 108a to block a portion of light to the user's eye (e.g., pinhole acuity), a lens 108b configured to simulate distance vision to the user's eye (e.g., distance acuity, such as the distance d1), a pass through selection 108c that enables unmodified vision to the user's eye (e.g., near visual acuity), and a filter 108d configured to filter light to the user's eye (e.g., another type of acuity). In some implementations, the plurality of vision modifiers 108 may include a plurality of lenses configured to simulate vision at different distances to the user's eye (e.g., intermediate vision).

In some implementations, the handheld device 200 may include a handle 122 to enable the user to hold the handheld device 200 against the user's face with one hand while the user is also holding the eye examination subsystem 104 (e.g., a smartphone or tablet) in another hand at an arm's length or while the eye examination subsystem 104 rests in a support stand. The handheld device 200 could also have a bridge that rests on the user's nose. In some implementations, the handheld device 200 may rotate a wheel, at a center point 124, to select between vision modifiers of the plurality of vision modifiers 108. In some cases, the handheld device 200 can automatically rotate the wheel, such as in response to a transmission received from the eye examination subsystem 104.

By way of example, the lens (e.g., the lens 108b) can simulate a greater distance (e.g., 20 feet) than exists between the user and the display 114 (e.g., the arm's length, such as 60 centimeters). The lens, when present, can be placed to cover the user's eyes (e.g., the tested eye, such as the right eye) to simulate distance vision between the user and the display 114 of the handheld device 200. One or more lenses can be configured in the handheld device 200 with different powers to simulate different distances between the user's face and the display 114. For example, the different powers of lenses may be used for different eye tests and/or utilization of different devices (e.g., desktops, laptops, smartphones, or tablet computers), which might require a different eye-to-device distance to account for their different screen resolutions. The lens (e.g., the lens 108b) may simulate a correct distance, based on the distance d1, when performing the eye examination. The system 100 may determine, via the camera 112, the distance d1 between the handheld device 200 and the display 114. The distance d1 may be determined based on comparing a fixed size of the visual indicator 106 to a detected size of the visual indicator 106. The system 100 may then output, via the display 114, an eye examination image for visual acuity based on the distance d1 being within a valid range. The eye examination image may include a visual stimulus having an output size which may be determined based on the distance d1. The system 100 may receive an input from the user, via the input device 116, indicating a selection of the visual stimulus. The system 100 may then generate an eye examination score based on the input.

Figure 4:
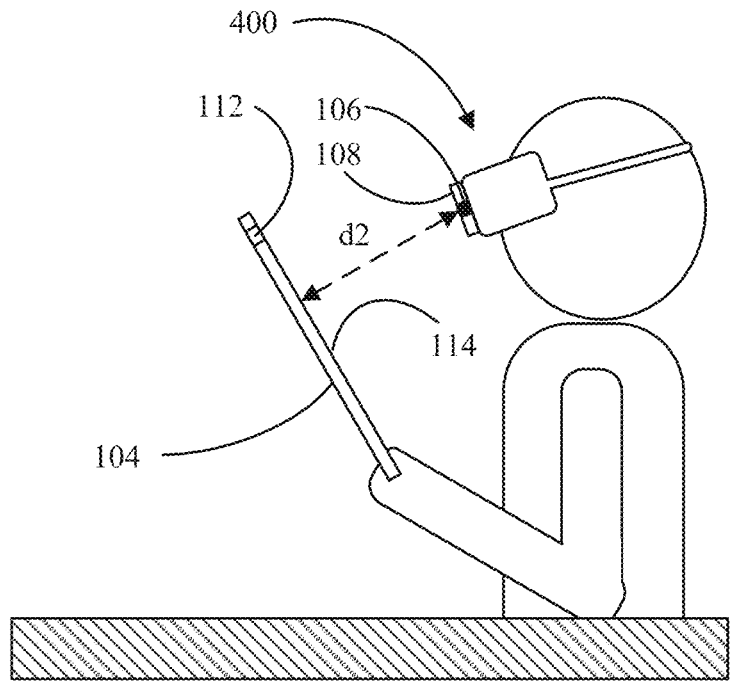
FIG. 4 is an example of utilizing an optical subsystem comprising a head worn device for conducting eye examinations for visual acuity.

In another example, with reference to FIG. 4, the user can utilize a head worn device 400 (e.g., a second variation of the optical subsystem 102) for conducting eye examinations. The head worn device 400 may enable the user to self-administer an eye examination, such as a visual acuity test, astigmatism test, or color test displayed via the display 114. The eye examination may require that one of the user's eyes remains open while the other of the user's eyes is closed. In some cases, the user may wear the head worn device 400 on their head while holding the eye examination subsystem 104 (e.g., the user device) within an arm's length or resting the eye examination subsystem 104 on a support stand. The system 100 may determine, via the camera 112, a distance d2 between the head worn device 400 and the display 114. The distance d2 may be determined based on comparing a fixed size of the visual indicator 106 to a detected size of the visual indicator 106 in an image obtained by the camera 112.

Figure 5:
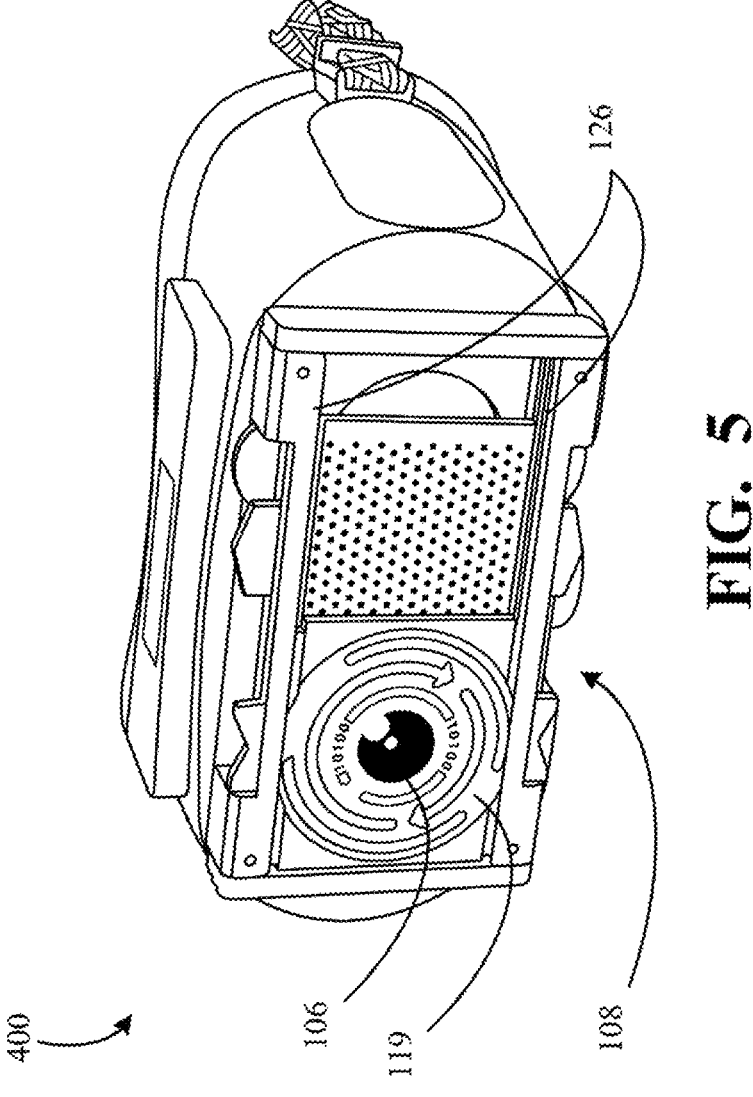
FIG. 5 is an example of a head worn device.

The head worn device 400 may include an opaque surface 119 that blocks light to one of the user's eyes. For example, as shown in FIG. 5, the right eye of the user may be occluded by an opaque surface 119. The head worn device 400 can help the user to ensure that the correct eye is properly closed (e.g., the untested eye, such as the right eye, via the opaque surface 119) when performing the eye examination. The head worn device 400 may include the plurality of vision modifiers 108 to modify vision of the user's other eye in different ways, such as a pass through (nothing), one or more occluders, one or more lenses, and/or one or more filters. For example, the plurality of vision modifiers 108 may include a pinhole occluder to block a portion of light to the user's eye (e.g., pinhole acuity), a lens configured to simulate distance vision to the user's eye (e.g., distance acuity, such as the distance d1), a pass through selection that enables unmodified vision to the user's eye (e.g., near visual acuity), and a filter configured to filter light to the user's eye. In some implementations, the plurality of vision modifiers 108 may include a plurality of lenses configured to simulate vision at different distances to the user's eye (e.g., intermediate vision).

In some implementations, the head worn device 400 may be configured with a strap to wrap around the user's head. In some implementations, the head worn device 400 may be configured as eyewear that include frames to rest on the user's face and arms to rest on the user's ears. For example, the head worn device 400 could be configured like a pair of eyeglasses. The head worn device 400 may be configured to slide one or more vision modifiers along a track 126 to select between different vision modifiers of the plurality of vision modifiers 108 for one or both eyes of the user. In some implementations, the head worn device 400 can automatically slide one or more vision modifiers along the track 126, such as in response to a transmission received from the eye examination subsystem 104.

By way of example, the lens can simulate a greater distance (e.g., 20 feet) than exists between the user and the display 114 (e.g., the arm's length, such as 60 centimeters). The lens, when present, can be placed to cover the other of the user's eyes (e.g., the tested eye, such as the left eye) to simulate distance vision between the user and the display 114 of the head worn device 400. One or more lenses can be configured in the head worn device 400 with different powers to simulate different distances between the user's face and the display 114. For example, the different powers of lenses may be used for different eye tests and/or utilization of different devices (e.g., desktops, laptops, smartphones, or tablet computers), which might require a different eye-to-device distance to account for their different screen resolutions. The lens can simulate a correct distance, based on the distance d2, when performing the eye examination. The system 100 may determine, via the camera 112, the distance d2 between the head worn device 400 and the display 114. The distance d2 may be determined based on comparing a fixed size of the visual indicator 106 to a detected size of the visual indicator 106 in an image obtained by the camera 112. The system 100 may then output, via the display 114, an eye examination image for visual acuity based on the distance d2 being within a valid range. The eye examination image may include a visual stimulus having an output size which may be determined based on the distance d2. The system 100 may receive an input from the user, via the input device 116, indicating a selection of the visual stimulus. The system 100 may then generate an eye examination score based on the input.

Referring again to FIG. 1, the system 100 may enable users to self-administer an eye examination for visual acuity. The display 114 may be used to output various stimuli (e.g., a Snellen chart having a series of letters of different sizes in different rows). For example, the system 100 may use the visual indicator 106 to determine the distance (e.g., the distance d1 or the distance d2), then dynamically change the size of the series of letters (e.g., scaling the Snellen chart), or if beyond the valid range, stop or suspend the eye examination. The user, following instructions on the display 114 while holding the handheld device 200 or wearing the head worn device 400 (e.g., placed in line of either or both eyes), can modify their vision for the eye testing. In some implementations, the user can select the vision modifier (e.g., via the optical subsystem 102), and the system 100 (e.g., the eye examination subsystem 104) can detect the selection and output an eye examination image to the display based on the selection. In some implementations, the system

100 (e.g., the eye examination subsystem 104) can select an eye examination image to display based on an eye examination to perform, then cause a vision modifier to be selected (e.g., causing the optical subsystem 102 to automatically switch to the vision modifier based on a transmission from the eye examination subsystem 104).

In some implementations, the eye examination subsystem 104, via the control system 118, can decode information encoded by the visual indicator 106. For example, the eye examination subsystem 104 can utilize the camera 112 to scan the QR code or barcode and/or to detect the letters, geometrical shapes, text, images, or colors. In some implementations, the control system 118 may access the data structure 120 to decode the information from the visual indicator 106. For example, the data structure 120 may comprise a look up table that correlates an identification number given by the visual indicator 106 to the information being decoded, such as identification of a selected vision modifier.

In some implementations, the plurality of vision modifiers 108 can be combined and placed in front of the user, without user intervention, by wired or wireless communication with the eye examination subsystem 104 (e.g., communication between the control system 110 and the control system 118). The eye examination subsystem 104 may determine, via the camera 112, a selection of a vision modifier of the plurality of vision modifiers 108. For example, the user may select a vision modifier, and the eye examination subsystem 104 may determine that selection based on a visual indicator 106 exposed due to the selection. In some cases, the eye examination subsystem 104 may output, via the display, the eye examination image based on a selection of a vision modifier of the plurality of vision modifiers 108. For example, selecting the vision modifier may cause the eye examination subsystem 104 to select an eye examination from a plurality of eye examinations. In some implementations, the eye examination subsystem 104 may transmit to the optical subsystem 102 a selection of a vision modifier of the plurality of vision modifiers 108. For example, the eye examination subsystem 104 may select a vision modifier from the plurality of vision modifiers 108 based on selection of an eye examination from a plurality of eye examinations. The optical subsystem 102 may select a vision modifier (e.g., via rotating the wheel at the center point 124, or sliding one or more vision modifiers along the track 126) based on a transmission received from the eye examination subsystem 104.

Figure 6:
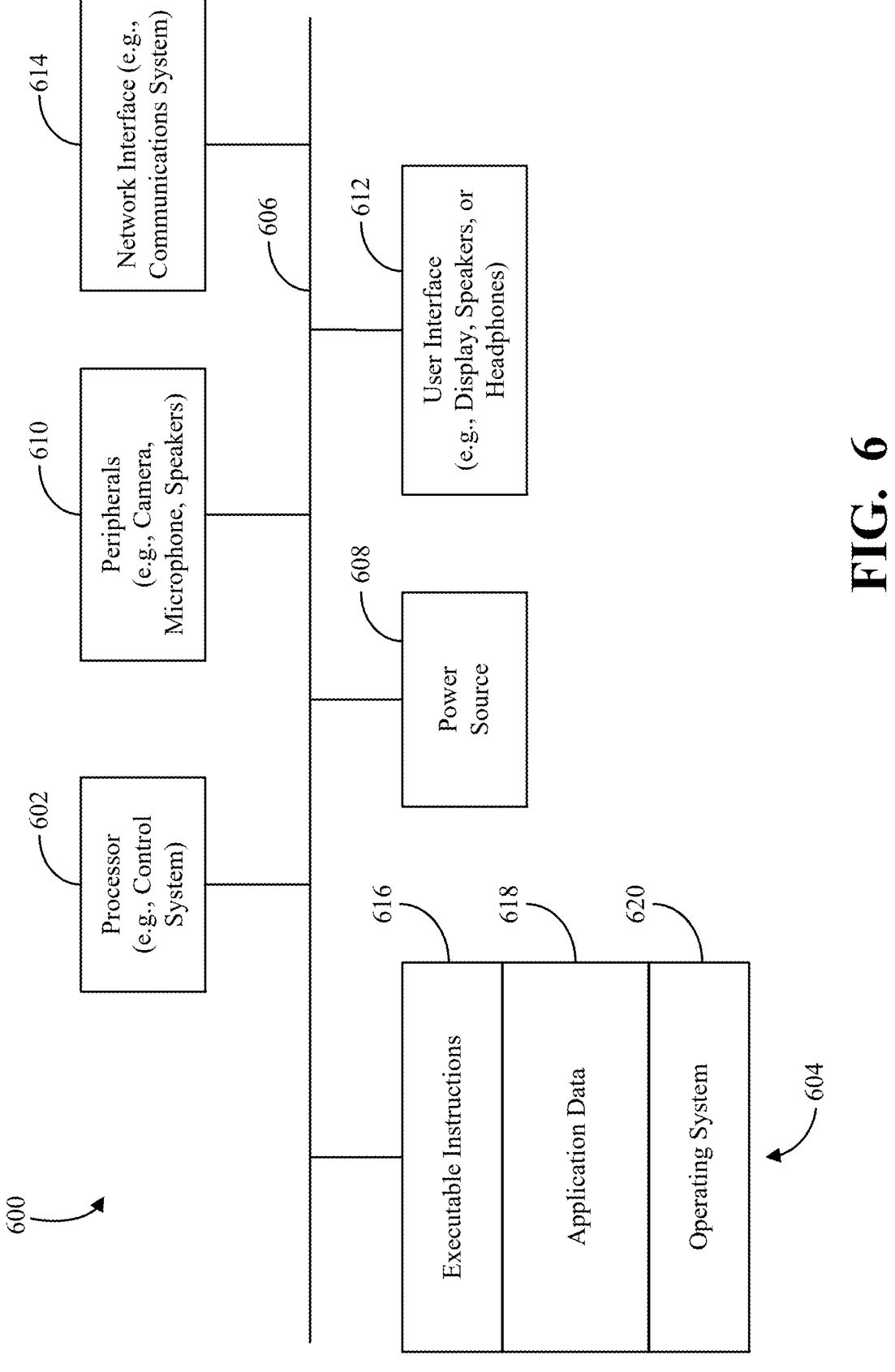
FIG. 6 is a block diagram of an example internal configuration of a computing device for conducting eye examinations for visual acuity.

FIG. 6 is a block diagram of an example internal configuration of a computing device 600 for conducting eye examinations for visual acuity. In one configuration, the computing device 600 may comprise the optical subsystem 102 (e.g., the handheld device 200 or the head worn device 400). In another configuration, the computing device 600 may comprise the eye examination subsystem 104 (e.g., a user device).

The computing device 600 includes components or units, such as a processor 602, a memory 604, a bus 606, a power source 608, peripherals 610, a user interface 612, a network interface 614, other suitable components, or a combination thereof. One or more of the memory 604, the power source 608, the peripherals 610, the user interface 612, or the network interface 614 can communicate with the processor 602 via the bus 606.

The processor 602 (e.g., the control system 110 or the control system 118) is a central processing unit, such as a microprocessor, and can include single or multiple processors having single or multiple processing cores. Alternatively, the processor 602 can include another type of device, or multiple devices, configured for manipulating or processing information. For example, the processor 602 can include multiple processors interconnected in one or more manners, including hardwired or networked. The operations of the processor 602 can be distributed across multiple devices or units that can be coupled directly or across a local area or other suitable type of network. The processor 602 can include a cache, or cache memory, for local storage of operating data or instructions.

The memory 604 includes one or more memory components, which may each be volatile memory or non-volatile memory. For example, the volatile memory can be random access memory (RAM) (e.g., a DRAM module, such as DDR DRAM). In another example, the non-volatile memory of the memory 604 can be a disk drive, a solid state drive, flash memory, or phase-change memory. In some implementations, the memory 604 can be distributed across multiple devices. For example, the memory 604 can include network-based memory or memory in multiple clients or servers performing the operations of those multiple devices.

The memory 604 can include data for immediate access by the processor 602. For example, the memory 604 can include executable control system 616, application data 618, and an operating system 620. The executable control system 616 can include one or more application programs, which can be loaded or copied, in whole or in part, from non-volatile memory to volatile memory to be executed by the processor 602. For example, the executable control system 616 can include instructions for performing some or all of the techniques of this disclosure. The application data 618 can include user data, database data (e.g., database catalogs or dictionaries), or the like. In some implementations, the application data 618 can include functional programs, such as a web browser, a web server, a database server, another program, or a combination thereof. The operating system 620 can be, for example, Microsoft Windows®, Mac OS X®, or Linux®; an operating system for a mobile device, such as a smartphone or tablet device; or an operating system for a non-mobile device, such as a mainframe computer.

The power source 608 provides power to the computing device 600. For example, the power source 608 can be an interface to an external power distribution system. In another example, the power source 608 can be a battery, such as where the computing device 600 is a mobile device or is otherwise configured to operate independently of an external power distribution system. In some implementations, the computing device 600 may include or otherwise use multiple power sources. In some such implementations, the power source 608 can be a backup battery.

The peripherals 610 (e.g., the camera 112 or microphone) includes one or more sensors, detectors, or other devices configured for monitoring the computing device 600 or the environment around the computing device 600. For example, the peripherals 610 can include a front facing built-in camera. In another example, the peripherals can include a plurality of cameras. In another example, the peripherals can include a range detection system, such as Lidar, for determining a distance to the user. In another example, the peripherals can include a geolocation component, such as a global positioning system location unit.

The user interface 612 includes one or more input interfaces and/or output interfaces. An input interface (e.g., the input device 116) may, for example, be a positional input device, such as a mouse, touchpad, touchscreen, or the like; a keyboard; or another suitable human or machine interface device. An output interface (e.g., the display 114) may, for example, be a display, such as a liquid crystal display, a cathode-ray tube, a light emitting diode display, virtual reality display, or other suitable display. In another example, the output interface may include speakers or headphones.

The network interface 614 (e.g., communications systems of the optical subsystem 102 or the eye examination subsystem 104) provides a connection or link to a network. The network interface 614 can be a wired network interface or a wireless network interface. The computing device 600 can communicate with other devices via the network interface 614 using one or more network protocols, such as using Ethernet, transmission control protocol (TCP), internet protocol (IP), power line communication, an IEEE 802.X protocol (e.g., Wi-Fi, Bluetooth, or ZigBee), infrared, visible light, general packet radio service (GPRS), global system for mobile communications (GSM), code-division multiple access (CDMA), Z-Wave, another protocol, or a combination thereof. In some cases, the network interface 614 may enable communication between the optical subsystem 102 and the eye examination subsystem 104. In some cases, the network interface 614 may enable communication with the data structure 120.

FIG. 7 is a flowchart of an example of a process 700 for conducting eye examinations for visual acuity. The process 700 can be executed using computing devices, such as the systems, hardware, and software described with respect to FIGS. 1-6. The process 700 can be performed, for example, by executing a machine-readable program or other computer-executable instructions, such as routines, instructions, programs, or other code. The operations of the process 700 or another technique, method, process, or algorithm described in connection with the implementations disclosed herein can be implemented directly in hardware, firmware, software executed by hardware, circuitry, or a combination thereof.

For simplicity of explanation, the process 700 is depicted and described herein as a series of operations. However, the operations in accordance with this disclosure can occur in various orders and/or concurrently. Additionally, other operations not presented and described herein may be used. Furthermore, not all illustrated operations may be required to implement a technique in accordance with the disclosed subject matter.

At operation 702, a system may utilize a depth estimation algorithm to determine, via a camera, a distance between an optical subsystem and a display. For example, the eye examination subsystem 104 (e.g., a user device, such as smartphone, tablet, or laptop computer) may determine, via the camera 112, a distance (e.g., the distance d1 or the distance d2) between the optical subsystem 102 (e.g., the handheld device 200 or the head worn device 400) and the display 114. The distance may be determined based on comparing a fixed size of a visual indicator (e.g., the visual indicator 106, such as a QR code, barcode, or other visual symbol, or an anatomic feature of the user) to a detected size of the visual indicator in an image obtained by the camera.

At operation 704, the system may determine a selection of a vision modifier from a plurality of vision modifiers and/or a selection of an eye examination from a plurality of eye examinations. For example, the system may determine a selection of a vision modifier from the plurality of vision modifiers 108 based on a selection of the eye examination from the data structure 120 corresponding to the vision modifier.

At operation 706, the system may determine whether the distance between the optical subsystem and the display is within a valid range for the eye examination. If the distance is not within the valid range (e.g., "No," such as the user being too close or too far away from the display), the process may return to operation 702 (e.g., waiting for a change in distance). In some cases, the system may output, via a speaker or the display of the system, an indication to the user to change the distance to within the valid range (e.g., to move closer to the display or further from the display). However, if the distance is within the valid range (e.g., "Yes," such as the user being within an established distance, which could be an arm's length), the process may continue to operation 708.

At operation 708, the system may, via the camera, determine whether one or both eyes of the user are covered for the eye examination. This may include determining that an occluder is in a correct position with an opaque surface covering one eye (e.g., the left eye) and/or a pass through (nothing), a partial or pinhole occluder, a lens, or a filter is in a correct position covering the other eye (e.g., the right eye). If one or both eyes of the user are not covered as may be required by the eye examination (e.g., "No"), the process may return to operation 702 (e.g., waiting for one or both eyes to be properly covered). However, if one or both eyes of the user are covered (e.g., "Yes"), the process may continue to operation 710.

At operation 710, the system may output an eye examination image for visual acuity (e.g., a Snellen chart) based on the distance being within the valid range and/or the one or both eyes being covered. The eye examination image may include a visual stimulus having an output size determined based on the distance. For example, the size of the visual stimulus (e.g., configured via resolution of the display) may be determined based on the distance. The system may configure a GUI to display the eye examination to the user. In some implementations, the system may determine the eye examination to administer based on a decoding of the visual indicator. In some implementations, the system may stop or suspend, via the display, output of the eye examination image based on the distance being greater than or less than the valid range. For example, the system may suspend the eye examination when the distance is greater than or less than the valid range, then resume the eye examination when the distance returns to being within the valid range.

At operation 712, the system may receive input from the user indicating selection of the visual stimulus and may generate an eye examination score based on the input. The system may output, via the display, speakers, or headphones, a result of the eye examination. In some implementations, the score may be based on information encoded by the visual indicator (e.g., indicating the eye examination being administered, and the power of lens being used) in addition to the input from the user (e.g., indicating a lowest line the user can read on the Snellen chart). In some implementations, the system may output a result of the eye examination as a confirmation (e.g., pass or fail) or score (e.g., percentage).

In utilizing the various aspects of the embodiments, it would become apparent to one skilled in the art that combinations or variations of the above embodiments are possible for conducting eye examinations for visual acuity. Although the embodiments have been described in language specific to structural features and/or methodological acts, it is to be understood that the appended claims are not necessarily limited to the specific features or acts described. The specific features and acts disclosed are instead to be understood as embodiments of the claims useful for illustration.

12

What is claimed is:

1. A system for conducting an eye examination for visual acuity, comprising:
   an optical subsystem configured to be positioned in front of one or both eyes of a user, the optical subsystem comprising i) a handheld device or ii) a head worn device, a visual indicator having a fixed size, and a plurality of vision modifiers configured to modify vision of the user;
   a camera;
   a display; and
   one or more processors configured by instructions stored in memory to:
      determine, via the camera, a distance between the optical subsystem and the display, the distance determined based on comparing the fixed size of the visual indicator to a detected size of the visual indicator in an image obtained by the camera;
      output, via the display, an eye examination image for testing visual acuity based on the distance being within a valid range, the eye examination image including a visual stimulus having an output size determined based on the distance; and
      receive an input from the user indicating a selection of the visual stimulus.

2. The system of claim 1, wherein the one or more processors are further configured by instructions stored in memory to:
   determine, via the camera, a selection of a vision modifier of the plurality of vision modifiers.

3. The system of claim 1, wherein the one or more processors are further configured by instructions stored in memory to:
   output, via the display, the eye examination image based on a selection of a vision modifier of the plurality of vision modifiers.

4. The system of claim 1, wherein the one or more processors are further configured by instructions stored in memory to:
   transmit, to the optical subsystem, a selection of a vision modifier of the plurality of vision modifiers for conducting the eye examination.

5. The system of claim 1, wherein the optical subsystem selects a vision modifier of the plurality of vision modifiers based on a transmission that is received from a device that includes the display.

6. The system of claim 1, wherein the visual indicator comprises an anatomic feature of the user.

7. The system of claim 1, wherein the visual indicator comprises a code that indicates a selection of a vision modifier of the plurality of vision modifiers.

8. The system of claim 1, further comprising:
   an input device configured to receive the input from the user, wherein the input device comprises at least one of a microphone, a touchscreen, an air mouse, or a laser device.

9. The system of claim 1, wherein the plurality of vision modifiers includes a pinhole occluder and a lens configured to simulate distance vision.

10. The system of claim 1, wherein the plurality of vision modifiers includes a plurality of lenses configured to simulate vision at different distances.

11. The system of claim 1, wherein the plurality of vision modifiers includes a filter configured to filter light to one or both eyes of the user.

12. The system of claim 1, wherein the plurality of vision modifiers includes a pass through selection that enables unmodified vision of the user.

13. The system of claim 1, wherein the eye examination image is configured for testing at least one of distance acuity, pinhole acuity, or near visual acuity.

14. The system of claim 1, wherein the handheld device is configured to rotate a wheel to select between vision modifiers of the plurality of vision modifiers for one or both eyes of the user.

15. The system of claim 1, wherein the head worn device is configured to slide a vision modifier along a track to select between vision modifiers of the plurality of vision modifiers for one or both eyes of the user.

16. The system of claim 1, wherein the camera, the display, and the one or more processors are integrated in smartphone, tablet, or laptop computer.

17. The system of claim 1, wherein the one or more processors are further configured by instructions stored in memory to:

determine the distance is greater than or less than the valid range; and output, via at least one of a speaker or the display, an indication to the user to change the distance to within the valid range.

18. The system of claim 1, wherein the handheld device or the head worn device is adapted to block vision of a first eye of the user while aligning a selectable one of the plurality of vision modifiers in front of a second eye of the user.

19. The system of claim 18, wherein the visual indicator is disposed on the handheld device or the head worn device and positioned in front of the first eye having blocked vision.

20. A method for conducting an eye examination for visual acuity, comprising:

determining, via a camera, a distance between an optical subsystem and a display, the optical subsystem configured to be positioned in front of one or both eyes of a user, the optical subsystem comprising I) a handheld device or ii) a head worn device, a visual indicator having a fixed size, and a plurality of vision modifiers configured to modify vision of the user, the distance determined based on comparing the fixed size of the visual indicator to a detected size of the visual indicator in an image obtained by the camera;

outputting, via the display, an eye examination image for testing visual acuity based on the distance being within a valid range, the eye examination image including a visual stimulus having an output size determined based on the distance; and receiving an input from the user indicating a selection of the visual stimulus.

21. The method of claim 20, further comprising:

determining, via the camera, at least one of a color or a quick response (QR) code corresponding to a selection of a vision modifier of the plurality of vision modifiers.

22. The method of claim 20, further comprising:

stopping, via the display, output of the eye examination image based on the distance being greater than or less than the valid range.

\* \* \* \* \*